(12) United States Patent
McKinnon et al.

(10) Patent No.: US 9,579,209 B2
(45) Date of Patent: Feb. 28, 2017

(54) CONSTRAINED KNEE PROSTHESIS

(71) Applicant: Smith & Nephew, Inc., Memphis, TN (US)

(72) Inventors: Brian William McKinnon, Bartlett, TN (US); Nathaniel Milton Lenz, Germantown, TN (US); Scott Kennedy Laster, Memphis, TN (US); Michael D. Ries, Tiburon, CA (US); Steven B. Haas, New York, NY (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/329,546

(22) Filed: Jul. 11, 2014

(65) Prior Publication Data

US 2014/0324176 A1    Oct. 30, 2014

Related U.S. Application Data

(62) Division of application No. 13/360,184, filed on Jan. 27, 2012, now Pat. No. 8,808,388.

(60) Provisional application No. 61/436,788, filed on Jan. 27, 2011.

(51) Int. Cl.
*A61F 2/38* (2006.01)
*A61F 2/46* (2006.01)

(52) U.S. Cl.
CPC ............ *A61F 2/3886* (2013.01); *A61F 2/384* (2013.01); *A61F 2/389* (2013.01); *A61F 2/3859* (2013.01); *A61F 2/3868* (2013.01); *A61F 2/4684* (2013.01)

(58) Field of Classification Search
CPC ....... A61F 2/3886; A61F 2/3868; A61F 2/389
See application file for complete search history.

(56) References Cited

U.S. PATENT DOCUMENTS

| 3,824,630 A | 7/1974 | Johnston |
| 4,209,861 A | 7/1980 | Walker et al. |
| 4,249,270 A | 2/1981 | Bahler et al. |

(Continued)

FOREIGN PATENT DOCUMENTS

| AU | 2005209244 | 9/2006 |
| EP | 0381352 | 8/1990 |

(Continued)

OTHER PUBLICATIONS

Zimmer, Insall/Burstein II Constrained Condylar: Modular Knee System, Surgical Technique, copyright 1989, 36 pages.

(Continued)

*Primary Examiner* — Thomas J Sweet
*Assistant Examiner* — Daniel Bissing
(74) *Attorney, Agent, or Firm* — Fish & Richardson P.C.

(57) ABSTRACT

A tibial insert includes a base and a post extending from the base along a longitudinal axis. The post has a medial surface, a lateral surface, and a height along the longitudinal axis. The medial surface has a medial section, and the lateral surface has a lateral section oriented substantially parallel to the medial section. The medial section and the lateral section each have a width in a substantially anterior-posterior direction that is sufficient to enable varus/valgus constraint over a flexion/extension range from extension to about 90 to 120 degrees of flexion when the tibial insert is mated with a femoral component.

22 Claims, 9 Drawing Sheets

(56) References Cited

U.S. PATENT DOCUMENTS

| | | | |
|---|---|---|---|
| 4,298,992 A * | 11/1981 | Burstein | A61F 2/3886 623/20.27 |
| 4,470,158 A | 9/1984 | Pappas et al. | |
| 4,714,472 A | 12/1987 | Averill et al. | |
| 4,721,104 A | 1/1988 | Kaufman et al. | |
| 4,770,663 A | 9/1988 | Hanslik et al. | |
| 4,822,365 A | 4/1989 | Walker et al. | |
| 4,950,297 A | 8/1990 | Elloy et al. | |
| 4,950,298 A | 8/1990 | Gustilo et al. | |
| 4,959,071 A | 9/1990 | Brown | |
| 5,007,933 A | 4/1991 | Sidebotham et al. | |
| 5,011,496 A | 4/1991 | Forte et al. | |
| 5,133,758 A | 7/1992 | Hollister | |
| 5,181,925 A | 1/1993 | Houston et al. | |
| 5,282,867 A | 2/1994 | Mikhail | |
| 5,326,361 A | 7/1994 | Hollister | |
| 5,370,699 A | 12/1994 | Hood et al. | |
| 5,387,240 A | 2/1995 | Pottenger et al. | |
| 5,658,342 A | 8/1997 | Draganich et al. | |
| 5,871,545 A | 2/1999 | Goodfellow et al. | |
| 5,997,577 A | 12/1999 | Herrington et al. | |
| 6,039,764 A | 3/2000 | Pottenger et al. | |
| 6,068,658 A | 5/2000 | Insall et al. | |
| 6,206,926 B1 | 3/2001 | Pappas | |
| 6,764,516 B2 | 7/2004 | Pappas | |
| 6,972,039 B2 | 12/2005 | Metzger et al. | |
| 7,060,101 B2 | 6/2006 | O'Connor et al. | |
| 7,413,577 B1 | 8/2008 | Servidio | |
| 8,382,847 B2 | 2/2013 | Wyss | |
| 2001/0001121 A1 | 5/2001 | Lombardo et al. | |
| 2002/0103541 A1 | 8/2002 | Meyers et al. | |
| 2003/0009232 A1 | 1/2003 | Metzger et al. | |
| 2004/0122522 A1 | 6/2004 | Kubein-Meesenburg et al. | |
| 2004/0243244 A1 * | 12/2004 | Otto | A61F 2/3836 623/20.27 |
| 2005/0143832 A1 * | 6/2005 | Carson | A61F 2/3886 623/20.28 |
| 2005/0192672 A1 | 9/2005 | Wyss et al. | |
| 2008/0004701 A1 | 1/2008 | Axelson et al. | |
| 2010/0161067 A1 | 6/2010 | Saleh et al. | |
| 2011/0040387 A1 | 2/2011 | Ries | |
| 2011/0066247 A1 | 3/2011 | Ries et al. | |
| 2011/0118847 A1 | 5/2011 | Lipman et al. | |
| 2012/0095564 A1 * | 4/2012 | Mihalko | A61F 2/38 623/20.27 |

FOREIGN PATENT DOCUMENTS

| | | |
|---|---|---|
| EP | 0510299 | 8/1995 |
| EP | 0916321 | 6/2003 |
| GB | 1409150 | 10/1975 |
| WO | WO2008039735 A1 | 4/2008 |
| WO | WO2013074700 A1 | 5/2013 |

OTHER PUBLICATIONS

Zimmer, Insall/Burnstein II, Modular Knee System, Surgical Technique, pp. ZH000109691-ZH000109710. (21 pages).

International Search Report and Written Opinion in International Application No. PCT/US2012/022958, mailed Sep. 28, 2012, 7 pages.

Partial Supplementary European Search Report for European Application No. 12739549.9, mailed Mar. 8, 2016.

Extended European Search Report for European Application No. 12739549.9, mailed Sep. 5, 2016.

* cited by examiner

CONSTRAINED KNEE PROSTHESIS

CROSS-REFERENCE TO RELATED APPLICATIONS

This application is a divisional of U.S. patent application Ser. No. 13/360,184, filed Jan. 27, 2012, now allowed, which claims priority from and the full benefit of U.S. Provisional Patent Application Ser. No. 61/436,788, filed Jan. 27, 2011, and titled "Constrained Knee Prosthesis." The entire contents of U.S. patent application Ser. No. 13/360, 184 and U.S. Provisional Patent Application Ser. No. 61/436,788 are incorporated herein by reference.

TECHNICAL FIELD

This disclosure relates to knee prostheses.

BACKGROUND

Total knee replacement systems often include a tibial implant and a femoral implant that replace the articular surfaces of the knee. Posterior-stabilized knee replacement systems can be used to replace the function of both the anterior cruciate ligament (ACL) and posterior cruciate ligament (PCL). In some instances, posterior-stabilized knee replacement systems include varus/valgus constraint to also replace the function of the medial collateral ligament (MCL) and the lateral collateral ligament (LCL). Although a constrained knee replacement system can provide needed stability, it often introduces biomechanical inefficiencies.

SUMMARY

In a general aspect, a tibial insert provides varus/valgus constraint and permits tibiofemoral rotation. The tibial insert includes a post having walls configured to engage a femoral component over a flexion/extension range from extension to about 90 to about 120 degrees flexion. The post has rounded edges that permit tibiofemoral rotation when the post is in contact with the femoral component.

In another general aspect, a tibial insert includes a base and a post extending from the base along a longitudinal axis. The post has a medial surface, a lateral surface, and a height along the longitudinal axis. The medial surface has a medial section, and the lateral surface has a lateral section oriented substantially parallel to the medial section. The medial section and the lateral section each have a width in a substantially anterior-posterior direction that is sufficient to enable varus/valgus constraint over a flexion/extension range from extension to about 90 to 120 degrees of flexion when the tibial insert is mated with a femoral component.

Implementations can include one or more of the following features. For example, the femoral component defines an opening for receiving the post between substantially parallel walls, the opening providing a clearance of approximately 0.005 inches to approximately 0.030 inches between the post and the substantially parallel inner walls when the post is received in the opening. The medial section and the lateral section each extend such that, along at least half of the height of the post, the width of the medial section and width of the lateral section in the substantially anterior-posterior direction at a given axial position along the longitudinal axis is between approximately one sixth and approximately two thirds of a largest width of the post in the substantially anterior-posterior direction at that axial position. The post has a proximal surface that is substantially flat and a notch defined in a superior anterior portion of the post. At least a portion of the notch is defined completely through the post along a medial-lateral direction. The medial section and the lateral section are substantially flat and are oriented along the substantially anterior-posterior direction. For substantially the entire height of the post, at a given axial position, the width of the medial surface and the width of the lateral surface in the substantially anterior-posterior direction are between approximately one sixth and two thirds of the largest width of the post in the substantially anterior-posterior direction at that axial position. The average length of the medial surface in an axial direction is more than twice the average length of the medial surface in the substantially anterior-posterior direction, and the average length of the lateral surface in an axial direction is more than twice the average length of the lateral surface in the substantially anterior-posterior direction. The post is twisted along the axis of the post such that a superior portion of the post is rotationally offset from an inferior portion of the post. The post is rotationally offset from the base such that the medial surface and the lateral surface are oriented at an angle with respect to medial and lateral sides of the base. The post has an anterior surface and a posterior surface, and the anterior surface and the posterior surface each have a convex portion. The post has rounded edges between the anterior surface and the medial and lateral surfaces and between the posterior surface and the medial and lateral surfaces. The rounded edges have a radius of between approximately 0.030 and 0.090 inches.

In another general aspect, a method of operation of a knee prosthesis includes permitting flexion/extension of the knee prosthesis over a flexion/extension range of approximately 0 to 150 degrees, constraining varus/valgus alignment of the knee prosthesis over a constrained flexion/extension range from extension to about 90 to 120 degrees of flexion, and rotating a tibial insert of the knee prosthesis relative to a femoral component of the knee prosthesis about a substantially superior-inferior axis of the tibial insert over at least a portion of the constrained flexion/extension range.

In another general aspect, a method of trialing a tibial insert of a knee prosthesis includes coupling a first tibial insert to a prepared tibia or a tibial tray, assessing the suitability of the knee prosthesis, and removing the first tibial insert from the prepared tibia or the tibial tray. The method includes coupling a second tibial insert to the prepared tibia or the tibial tray. The second tibial insert is configured to permit flexion/extension of the knee prosthesis over a flexion/extension range of approximately 0 to 150 degrees, constrain varus/valgus alignment of the knee prosthesis over a constrained flexion/extension range from extension to about 90 to 120 degrees of flexion when the tibial insert mated with a femoral component, and rotate the tibial insert of the knee prosthesis relative to the femoral component about a substantially superior-inferior axis of the tibial insert over at least a portion of the constrained flexion/extension range.

Implementations can include one or more of the following features. For example, the first tibial insert and the second tibial insert each have a post, and the first tibial insert and the second tibial insert have differing post dimensions.

In another general aspect, a prosthesis includes a femoral component that defines an opening between substantially parallel inner walls and a tibial insert having a base and a post extending from the base. The post has a medial surface and a lateral surface, and is configured to be received in the opening. The medial surface has a medial section, and the lateral surface has a lateral section oriented substantially parallel to the medial section. The medial section and the lateral section each have a width in a substantially anterior-posterior direction that is sufficient to constrain varus/valgus alignment of the prosthesis over a flexion/extension range from extension to about 90 to 120 degrees of flexion when the tibial insert is mated with the femoral component such that the post is received in the opening and the medial section and the lateral section each engage one of the substantially parallel inner walls. Engagement of the tibial insert and the femoral component rotates the tibial insert relative to the femoral component over at least a portion of the constrained flexion/extension range.

Implementations can include one or more of the following features. For example, the post is dimensioned to provide a total clearance of approximately 0.005 to approximately 0.030 inches between the post and the substantially parallel inner walls when the post is received in the opening. The post has a posterior surface and an anterior surface, and the post has rounded edges between the anterior surface and the medial and lateral surfaces and between the posterior surface and the medial and lateral surfaces. The base has a medial bearing surface having a concave portion and a lateral bearing surface having a concave portion. The concave portion of the medial bearing surface is positioned anteriorly offset from a center of the base and has a maximum depth in a superior-inferior direction that is more inferior than a maximum depth of the concave portion of the lateral bearing surface in the superior-inferior direction. The post has a posterior surface, and the femoral component has an asymmetrical posterior cam configured to engage the posterior surface to drive rotation of the tibial insert relative to the femoral component. The posterior cam is configured to engage the posterior surface at angles of flexion that are greater than a first angle that is between approximately 60 and approximately 90 degrees of flexion, and the posterior cam is configured to not engage the posterior surface at angles of flexion less than the first angle.

The details of one or more implementations are set forth in the accompanying drawings and the description below. Other features, objects, and advantages of the disclosure will be apparent from the description, the drawings, and the claims.

DETAILED DESCRIPTION

Figure 1:
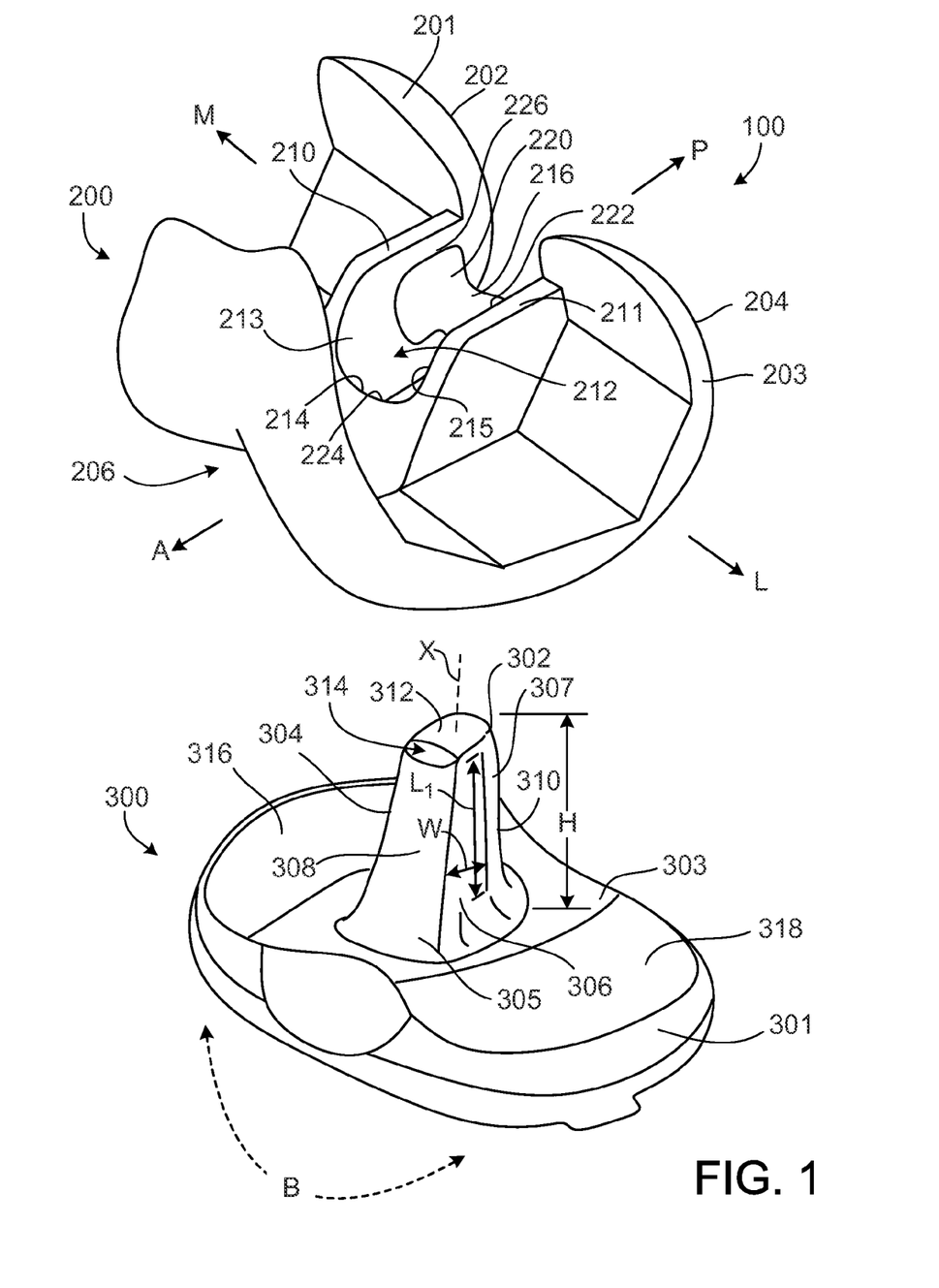
FIG. 1 is an exploded perspective view of a tibial insert and a femoral component of a left knee prosthesis.
Figure 2:
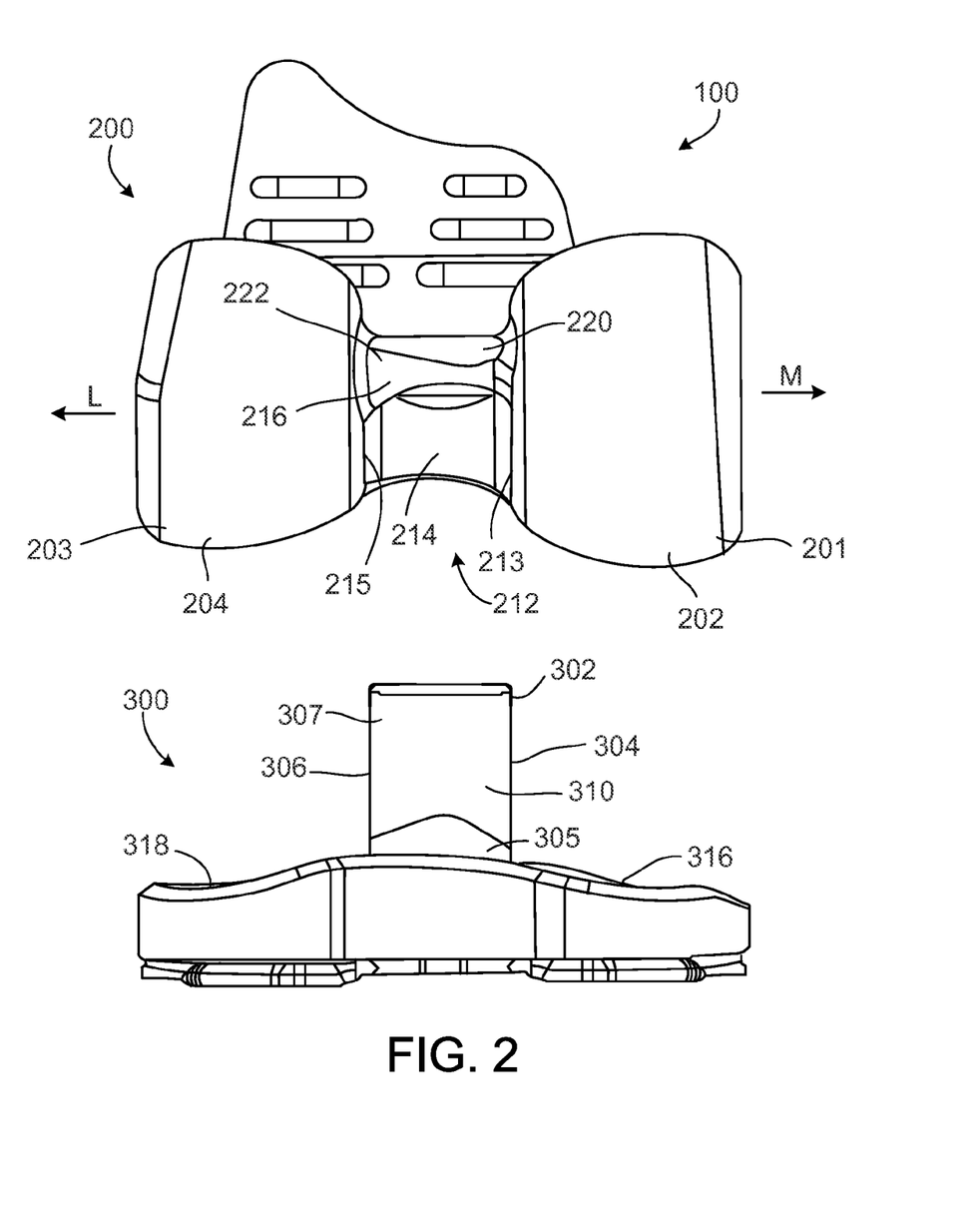
FIG. 2 is an exploded posterior view of the tibial insert and the femoral component.

Referring to FIGS. 1 and 2, a knee prosthesis 100 provides varus/valgus constraint and also permits internal and external rotation of the tibia relative to the femur. To achieve this, the knee prosthesis 100 includes a tibial insert 300 shaped to engage a femoral component 200 to (i) limit varus-valgus deviation of the tibia from its proper alignment with the femur, and (ii) facilitate rotation of the tibia relative to the femur during flexion. The tibial insert 300 can be referred to as a constrained insert, being constrained by the femoral component 200 in the assembled knee prosthesis 100.

During flexion of a healthy knee, the tibia rotates a small amount about its longitudinal axis (internal-external rotation). The knee prosthesis 100 enables this rotation helping to preserve a natural feel to the reconstructed knee. Internal rotation of the tibia relative to the femur (tibiofemoral rotation) aligns the line of action of the quadriceps and the tibia, improving the efficiency the quadriceps compared to an unaligned knee system. Proper alignment also reduces sheer forces on the patella and can improve the longevity of the knee prosthesis 100. The tibia rotates internally relative to the femur as the knee is flexed, and rotates externally relative to the femur as the knee is extended. The knee prosthesis 100 can also replace the function of the MCL and/or LCL in addition to the functions of the ACL and PCL, with the tibial insert 300 restricting varus/valgus forces on the knee.

In general, the possible movements of a tibia relative to a femur can be considered to include movements about three different axes. As a result of flexion and extension of the knee, the tibia moves relative to the femur about a medial-lateral axis through the knee. Varus/valgus motion refers to movement of the tibia and the femur about an anterior-posterior axis through the knee, for example, movement that causes the leg to bow medially or laterally. Axial rotation of the femur can occur relative to a longitudinal axis of the tibia (for example, an axis parallel to the shaft of the tibia, such as an axis along a substantially superior-inferior direction).

As used herein, tibiofemoral rotation refers to the axial rotation of the femur with respect to the longitudinal axis of the tibia, commonly referred to as internal and external rotation. In use, the knee prosthesis 100 restricts varus/valgus movement (for example, constrains varus/valgus movement to a particular range of motion or laxity) while causing tibiofemoral rotation to occur during flexion and extension.

The knee prosthesis 100 for a left knee includes the femoral component 200 for mounting to a distal end of a femur and the tibial insert 300 for attachment to a proximal end of a tibia. The tibial insert 300 can be attached to the tibia by known methods.

The femoral component 200 includes medial and lateral walls 210, 211 that define an opening 212 in the femoral component 200. The walls 210, 211 include substantially flat, substantially parallel inner surfaces 213, 215. Located at the anterior portion 224 of the walls 210, 211, the femoral component 200 includes an anterior cam 214 (FIG. 2). The femoral component 200 also includes a posterior cam 216 located at a superior posterior portion 226 of the walls 210, 211. The posterior cam 216 includes an uneven thickness, such that a lateral portion 222 of the posterior cam 216 is thicker than a medial portion 220.

The femoral component 200 includes a medial condylar portion 201 with a medial condylar surface 202. The femoral component also includes a lateral condylar portion 203 and a lateral condylar surface 204. The medial condylar surface 202 and the lateral condylar surface 204 are rounded, and in some implementations, can be asymmetrical. Between the medial condylar surface 202 and the lateral condylar surface 204, the femoral component 200 defines a trochlear groove 206 over which a patella or a patellar implant can glide during flexion of the knee.

The tibial insert 300 includes a base 301 and a raised section or post 302, extending from a substantially central location of a proximal surface 303 of the tibial insert 300. The post 302 extends from the base along a longitudinal axis, X, for example, an axis that extends in a substantially superior-inferior direction. The post 302 includes a medial surface 304, a lateral surface 306, an anterior surface 308, a posterior surface 310, and a proximal surface 312. When the femoral component 200 and the tibial component 300 are coupled, the post 302 is received within the opening 212 between the anterior cam 214 and the posterior cam 216. The medial surface 304 and the lateral surface 306 include substantially parallel, substantially flat contact sections 322, 320 (FIGS. 6 and 7) to contact the inner surfaces 213, 215 of the walls 210, 211 of the femoral component 200. The anterior surface 308 is convex in an anterior direction and the posterior surface 310 is convex in a posterior direction.

The proximal surface 312 is substantially flat, and the post 302 defines a notch 314, or patella relief, at its superior anterior portion. The notch 314 provides clearance for the patella or a patellar implant in deep flexion. The notch 314 may have a spherical radius similar to the spherical radius of patella implants available for use in the implant system. At least a portion of the notch 314 is defined completely through the post 302 along a substantially medial-lateral direction, for example, from the medial surface 304 to the lateral surface 306.

The tibial insert 300 also includes a medial bearing surface 316 and a lateral bearing surface 318 having sloped, concave portions that engage the medial condylar surface 202 and the lateral condylar surface 204, respectively.

The tibial insert 300 can be formed, for example, of high molecular weight polyethylene. Tibial trial inserts can be made of a sterilizable plastic, for example, a thermoplastic such as polyoxymethylene (acetal). Tibial trial inserts approximate the shape and dimensions of corresponding tibial inserts for implantation. Generally, the tibial trial inserts can be sterilized for reuse.

As described further below, in some implementations, the knee prosthesis 100 permits flexion/extension over a flexion/extension range of approximately 0 to 150 degrees of flexion. The knee prosthesis 100 constrains varus/valgus alignment of the knee prosthesis 100 over a constrained flexion/extension range from extension (or hyperextension) to about 90 to 120 degrees of flexion. In use, the tibial insert 300 rotates relative to the femoral component 200, resulting in tibiofemoral rotation over at least a portion of the constrained flexion/extension range. The tibial insert 300 and the femoral component 200 can rotate relative to each other over one or more portions of the constrained flexion/extension range or over the entire constrained flexion/extension range. The tibiofemoral rotation optionally occurs over a flexion/extension range of approximately 0 to 150 degrees of flexion. The rotation occurs about the axis of the tibia, which is in a direction about a substantially superior-inferior axis of the tibial insert such as the longitudinal axis, X, of the post 302. Translation of the tibial insert 300 relative to the femoral component 200 can also occur during the rotation, as described below.

Constraining varus/valgus alignment of the knee prosthesis 100 includes, for example, resisting medial and lateral forces on the knee prosthesis 100. In this manner, the knee prosthesis 100 supplements or replaces the functions of the MCL and/or the LCL. The knee prosthesis 100 can limit the varus/valgus alignment to a range of acceptable alignments, or limit deviation from a particular varus/valgus alignment to a predetermined range. In use, for example, the knee prosthesis 100 constrains the tibia and femur to a predetermined range of positions or range of angles relative to each other. The knee prosthesis 100 can provide constraint while permitting some varus/valgus movement of the knee within the predetermined range. The knee prosthesis 100 can constrain varus/valgus alignment or varus/valgus movement or to a range the same as or similar to a range of varus/valgus alignments or varus/valgus movement typical of healthy knees. In some implementations, the knee prosthesis 100 restricts varus/valgus deviation of the tibia and the femur to a total of 5 degrees or less, or a total of 1 degree or less, from a desired laxity. The desired varus/valgus laxity range of motion can be approximately 5 degrees. In some implementations, varus/valgus movement may be disallowed entirely.

During surgery to implant the knee prosthesis 100, a physician couples a tibial trial insert to a prepared tibia or tibial tray. The physician assesses the suitability of the size of the tibial trial insert by, for example, coupling and removing various tibial trial inserts to identify a tibial insert 300 most appropriate for the patient. The physician can perform a trial range of motion of the knee prosthesis 100 using a tibial trial insert. This permits the physician to assess the performance and stability of the tibial trial insert and to evaluate the behavior and function of ligaments and other tissues in cooperation with the knee prosthesis 100. The physician can assess, for example, whether the tibial trial insert sufficiently constrains varus/valgus alignment for the patient when engaged with the femoral component, and whether the tibial trial insert permits a sufficient range of tibiofemoral rotation.

As an example, a physician may trial a tibial trial insert that does not constrain varus/valgus motion or position, but permits flexion/extension over a flexion/extension range of approximately 0 to 150 degrees and rotates the tibial insert relative to the femoral component over a portion of or all of a flexion/extension range of approximately 0 to 150 degrees.

Through the trialing process, the physician may determine that additional constraint is appropriate. For example, the physician may determine that the patient presents with a lax or over-released medial collateral ligament (MCL). In response, the physician can trial a variety of tibial trial inserts that constrain varus/valgus alignment and also permit tibiofemoral rotation. The tibial trial inserts can have varying post 302 dimensions or varying dimensions of contact portions 320, 322, to provide varying levels of varus/valgus constraint and varying ranges of tibiofemoral rotation. For example, the physician may trial one or more different tibial trial inserts that each constrain varus/valgus alignment over a constrained flexion/extension range from extension (or hyperextension) to about 90 to 120 degrees flexion, permit flexion/extension over a flexion/extension range of approximately 0 to 150 degrees, and rotate relative to a femoral component over at least a portion of the constrained range when mated to the femoral component.

After a tibial trial insert has been determined to have an appropriate size and performance characteristics, the physician removes the tibial trial insert and in its place, couples a tibial insert 300 having the same size and features as the tibial trial insert to the tibia or tibial tray.

In some implementations, a library of tibial trial inserts (for example, a set of multiple tibial trial inserts) is provided for use during surgery. The tibial trial inserts in the library can have different post dimensions. For example, different tibial trial inserts can have different clearances relative to the femoral component 200, resulting in different levels of stability and tibiofemoral rotation. Additionally or alternatively, the different tibial trial inserts can also have different radii of curvature at the corners of the post, different post heights, different widths or shapes of medial and lateral surfaces (e.g., different contact sections 322, 320), different medial and lateral bearing surfaces, and other variations. Information about the stability and tibiofemoral rotation characteristics of the tibial trial inserts in the library are provided to the surgeon. The surgeon selects a trial insert from the library to achieve an appropriate balance of stability and tibiofemoral rotation for a particular patient. For example, the surgeon selects one or more tibial trial inserts that have stability and tibiofemoral rotation characteristics that match the needs indicated by patient data.

The level of stability (for example, the degree of stabilization or constraint) needed in the reconstructed knee can be predicted using pre-surgical laxity data, for example, data that indicates a relationship between an applied load and the resulting varus-valgus rotation of the knee. A load can be applied by, for example, a device attached to the patient or by a medical professional with a hand-held load measuring instrument. A desired amount of tibiofemoral rotation for the reconstructed knee can also be determined using pre-surgical data. For example, imaging techniques, such as magnetic resonance imaging (MRI), computed tomography (CT), and X-ray imaging, can be used to measure changes in a distance between the tibia and femur at different positions of the knee. Motion of the knee can also be tracked using image-based motion capture techniques, electromagnetic motion capture techniques, or mechanical linkages attached to the knee to measure the angular changes in knee position.

In the assembled knee prosthesis 100, engagement between the post 302 and the walls 210, 211 constrains varus/valgus alignment by limiting medial and lateral deviation of the tibial insert 300, that is, limiting tilting of the tibial insert 300 relative to the femoral component 200 in the direction of arrow B. To provide effective constraint, the contact sections 322, 320 of the medial surface 304 and the lateral surface 306 have a length, $L_1$, of, for example, between approximately 0.550 and approximately 0.870 inches. The walls 210, 211 of the femoral component 200 have a height in a superior-inferior direction that is, for example, at least as long as the length, $L_1$.

In addition, the contact sections 322, 320 have a width, W, in an anterior-posterior direction, for example, between approximately 0.125 and approximately 0.225 inches. The contact sections 322, 320 have a somewhat rectangular shape, so that the width, W, of the contact sections 322, 320 at the superior portion 307 of the post 302 is substantially the same as the width at the inferior portion 305 of the post 302. The width, W, is sufficient to enable varus/valgus constraint over a flexion/extension range from extension (or hyperextension) to about 90 to 120 degrees flexion when the tibial insert 300 is mated with the femoral component 200.

The contact sections 322, 320 optionally have a somewhat trapezoidal shape. For example, a largest anterior-posterior width of the contact sections 322, 320 can be located at an inferior portion of the contact sections 322, 320, and the anterior-posterior width can decrease in a superior direction from the largest width. A posterior boundary or edge of the contact sections 322, 320 can extend in a substantially superior-inferior direction, such that the changing anterior-posterior width results in a sloped anterior boundary or edge.

The height, H, of the post 302 and the length, $L_1$, of the contact sections 322, 320 affect the degree of varus/valgus constraint achieved. A higher post 302 provides contact with the walls 210, 211 over a greater distance along the length of the post 302, providing more effective constraint. Consequently, in some implementations, the post 302 is substantially the same height as the walls 210, 211. In some implementations, the height, H, of the post 302 is between approximately 0.720 and 0.990 inches.

In extension of the knee, the anterior surface 308 of the post 302 may engage the anterior cam 214 to provide anterior stabilization. Also, in extension, the contact sections 322, 320 can contact the walls 210, 211 to provide varus/valgus constraint at angles of flexion between extension or hyperextension and approximately 90 to 120 degrees. By contrast, in flexion of the knee, for example, at angles of flexion of approximately 125 degrees and higher, the medial surface 304 and lateral surface 306 would no longer be fully constrained between the walls 210, 211.

Extension corresponds to a position in which a leg is straight, for example, at zero degrees of flexion. Hyperextension is bending of the knee in the opposite direction of flexion, for example, bending the leg backward past full extension by some amount. As described above, the prosthesis can provide varus/valgus constraint over a range that includes hyperextension, for example, 1 degree, 5 degrees, or more of hyperextension.

Figure 3:
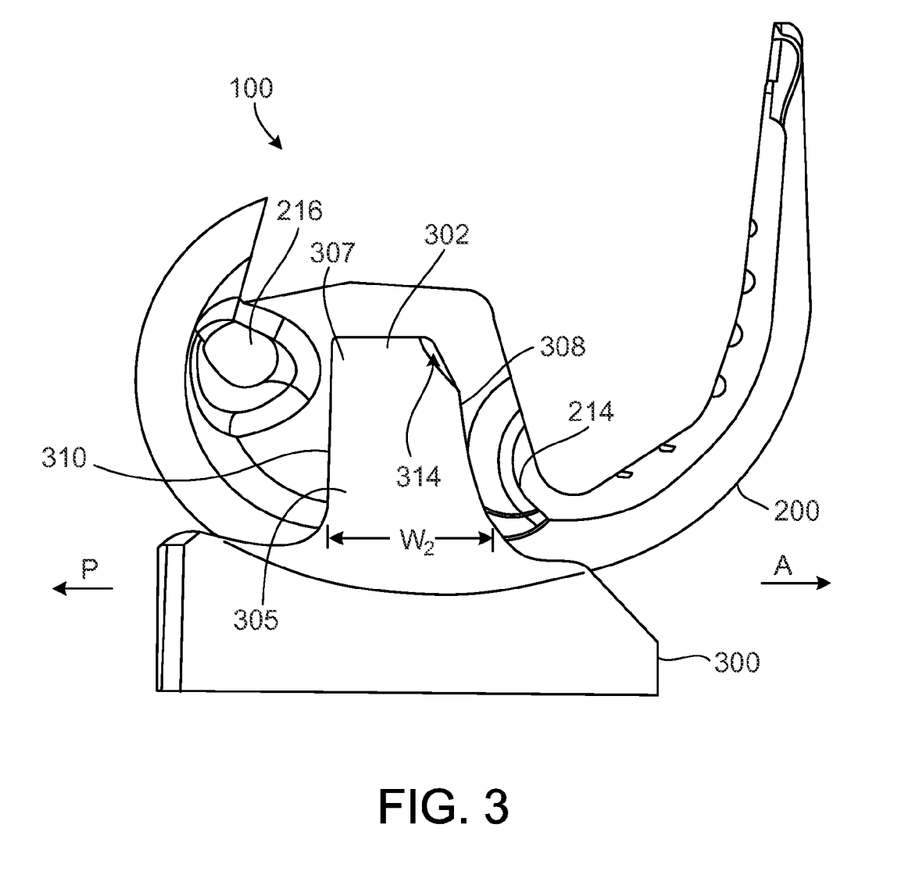
FIG. 3 is a sagittal section view of the tibial insert and the femoral component in extension.

As shown in FIG. 3, post 302 has a wider width, $W_2$, at the inferior portion 305 than at the superior portion 307. The increased anterior-posterior width strengthens the connection of the base 301 to the post 302. The width, $W_2$, also enables the anterior surface 308 to engage the anterior cam 214.

Figure 4:
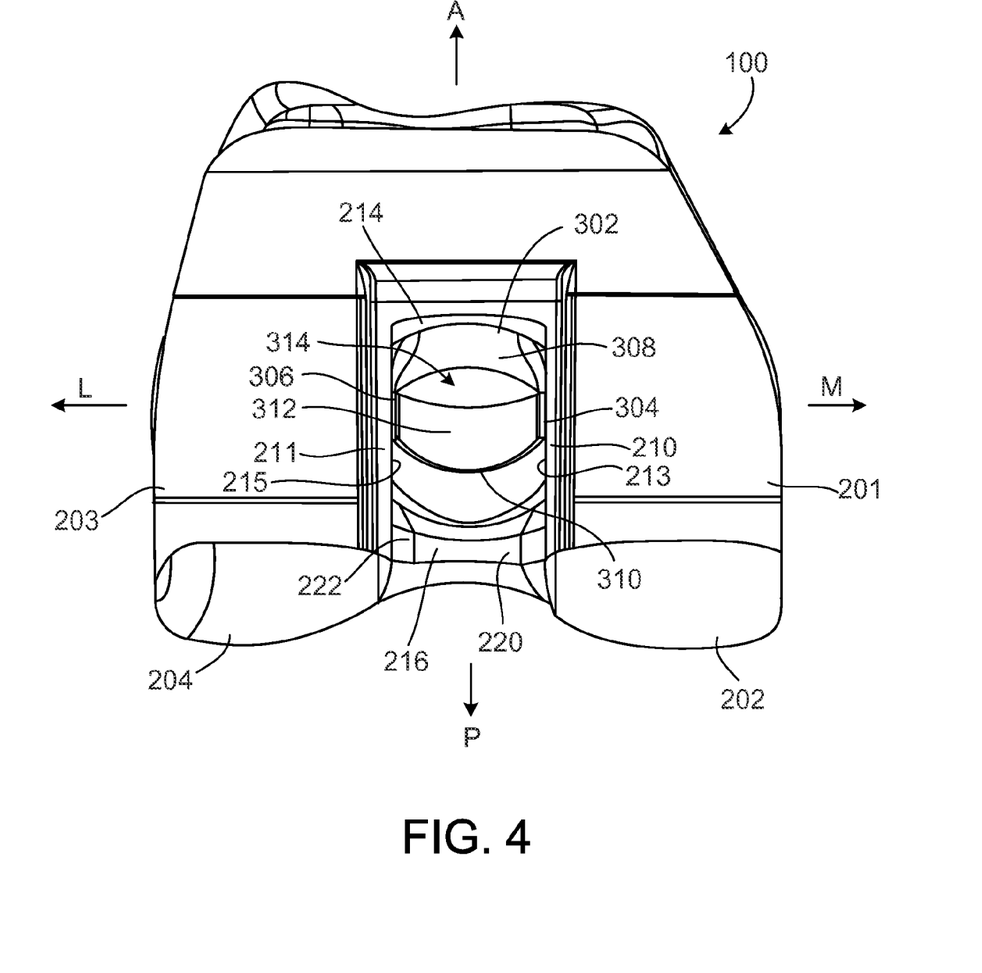
FIG. 4 is a top view of the tibial insert and the femoral component in extension.

FIG. 4 shows a top view of the knee prosthesis 100 in extension. From this position, as the knee flexes, the medial condylar surface 202 and the lateral condylar surface 204 roll and also glide over the medial bearing surface 316 and the lateral bearing surface 318, respectively. At flexion of approximately 60 to 90 degrees, the posterior cam 216 contacts the posterior surface 310 of the post 302 to provide posterior stabilization. Through continued flexion, the posterior cam 216 engages the posterior surface 310 of the post 302.

Thus, in some implementations, the posterior cam 216 is configured to engage the posterior surface 310 at a first angle that is between approximately 60 and 90 degrees of flexion, and at angles of flexion that are greater than the first angle. The posterior cam 216 is configured to not engage the posterior surface 310 at angles of flexion less than the first angle.

Internal rotation of the tibia relative to the femur occurs as the knee flexes between full extension and approximately 130 degrees of flexion. Tibiofemoral rotation is achieved by asymmetrical translation of the lateral condylar portion 203 compared to the medial condylar portion 201 relative to the tibial insert 300. In general, the lateral condylar portion 203 translates over a greater range than the medial condylar portion 201, resulting in rotation of the femoral component 200 relative to the tibial insert 300.

The asymmetric translation that drives tibiofemoral rotation is promoted by two mechanisms: first, the engagement of the bearing surfaces 316, 318 with the condylar surfaces 202, 204; and second, engagement of the asymmetrically-shaped posterior cam 216 with the posterior surface 310 of the post 302. These mechanisms result in the lateral condylar portion 203 of the femoral component sliding farther in a posterior direction than the medial condylar portion 201, relative to the tibial insert 300. Conversely, when moving toward extension, the lateral condylar portion 203 of the femoral component slides farther in an anterior direction than the medial condylar portion 201, relative to the tibial insert 300. This anterior translation during extension brings the anterior surface 308 of the post 302 near the anterior cam 214, where it may contact the post 302 if necessary to provide anterior stability. In some implementations, clearance is provided such that the anterior cam 214 does not contact the post 302 during normal standing, for example, with the leg straight at 0 degrees of flexion.

Differences between the medial bearing surface 316 and the lateral bearing surface 318 cause asymmetrical translation of the medial condylar surface 202 and the lateral condylar surface 204. For example, the medial bearing surface 316 is more concave (for example, extends deeper toward the inferior end of the tibial insert 300) than the lateral bearing surface 318. In other words, the lateral bearing surface 318 includes a larger radius of curvature than the medial bearing surface 316, and the generally shallower slope of the lateral bearing surface 318 facilitates greater travel of the lateral condylar portion 203 than that of the medial condylar portion 201.

The asymmetry of the posterior cam 216 also drives increased translation of the lateral condylar portion 203. At flexion between 0 degrees and approximately 60 to 90 degrees, before the posterior cam 216 engages the posterior surface 310 of the post 302, tibiofemoral rotation is promoted by the engagement of the condylar surfaces 202, 204 and the bearing surfaces 316, 318. As noted above, the lateral portion 222 of the posterior cam 216 is thicker than the medial portion 220 of the posterior cam 216. Once the posterior cam 216 engages the posterior surface 310 (for example, at approximately 60 to 90 degrees of flexion), the engagement of the thicker lateral portion 222 of the posterior cam 216 with the posterior surface 310 of the post 302 directs more force in the posterior direction on the lateral side of the femoral component 200, resulting in translation of the lateral condylar portion 203 that is greater than the translation of the medial condylar portion 201.

Figure 5:
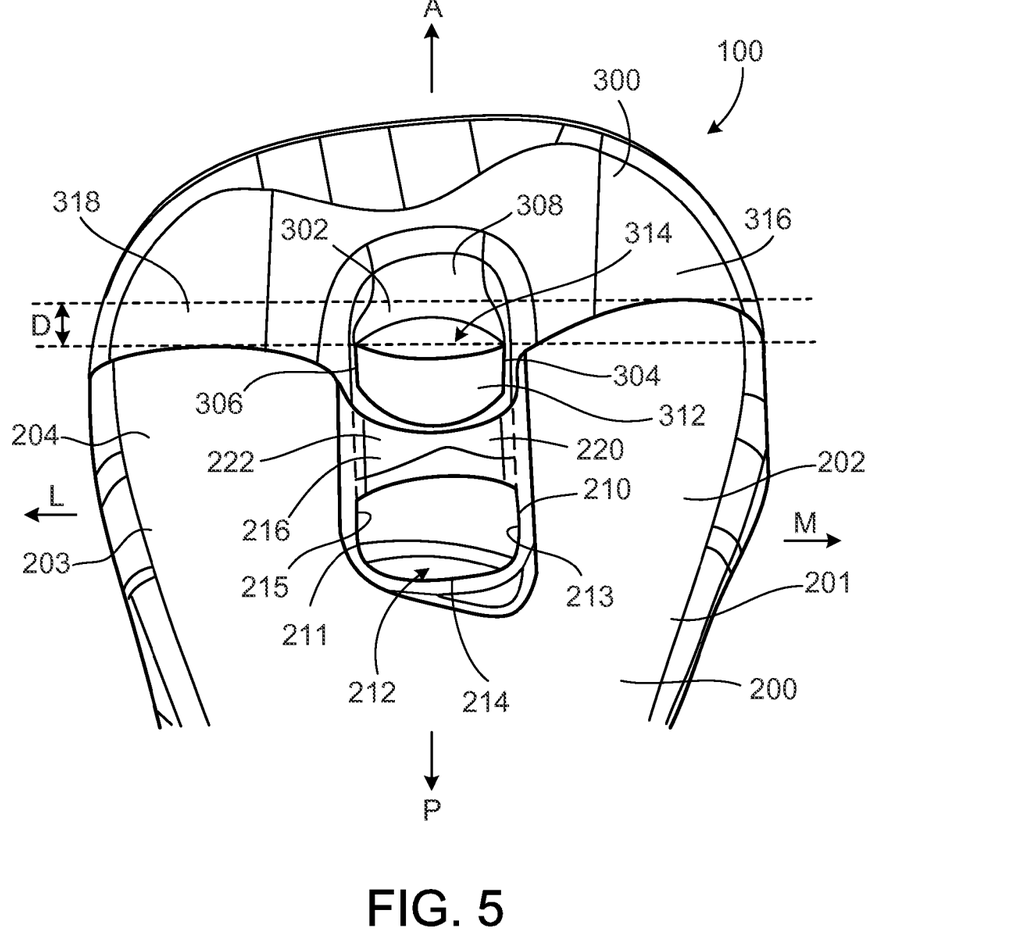
FIG. 5 is a top view of the tibial insert and the femoral component in flexion.

Referring to FIG. 5, with the knee shown at approximately 150 degrees of flexion, the lateral condylar portion 203 has translated more posteriorly than the medial condylar portion 201 resulting in tibiofemoral rotation. The difference in posterior translation is shown by distance D, which, for example, can correspond to rotation of the femoral component 200 relative to the tibial insert 300 of approximately 6 degrees or more. As shown, the medial surface 304 and the lateral surface 306 no longer contact the walls 210, 211, and thus do not provide varus/valgus constraint of the knee at this position.

Figure 6:
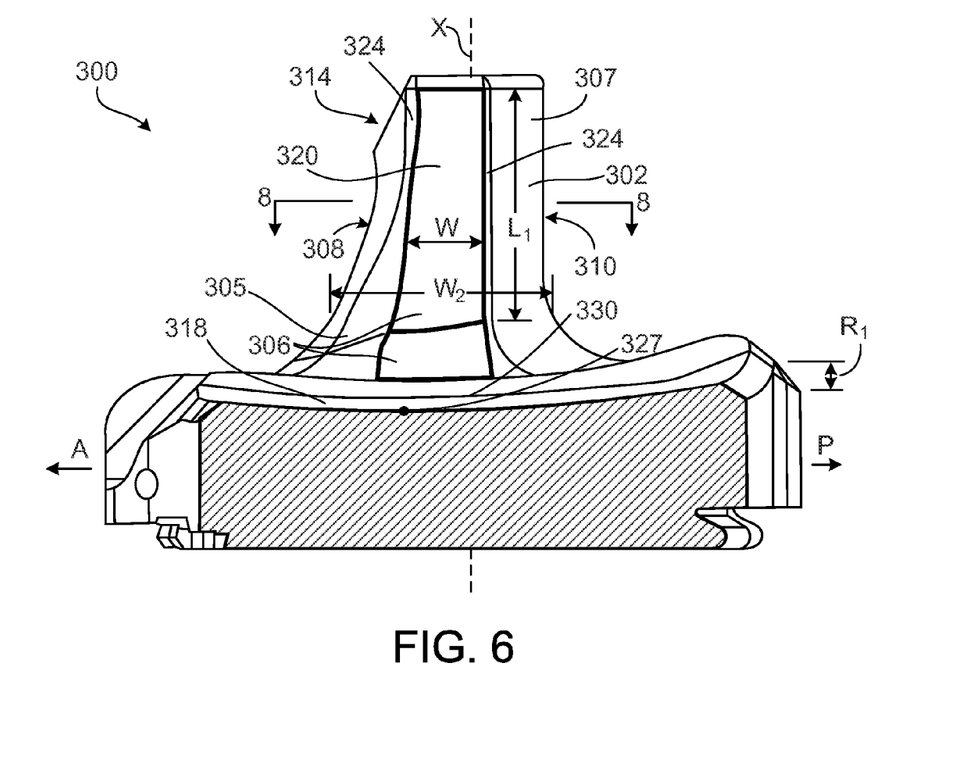
FIG. 6 is a lateral view of the tibial insert showing a cross section of a lateral bearing surface.
Figure 7:
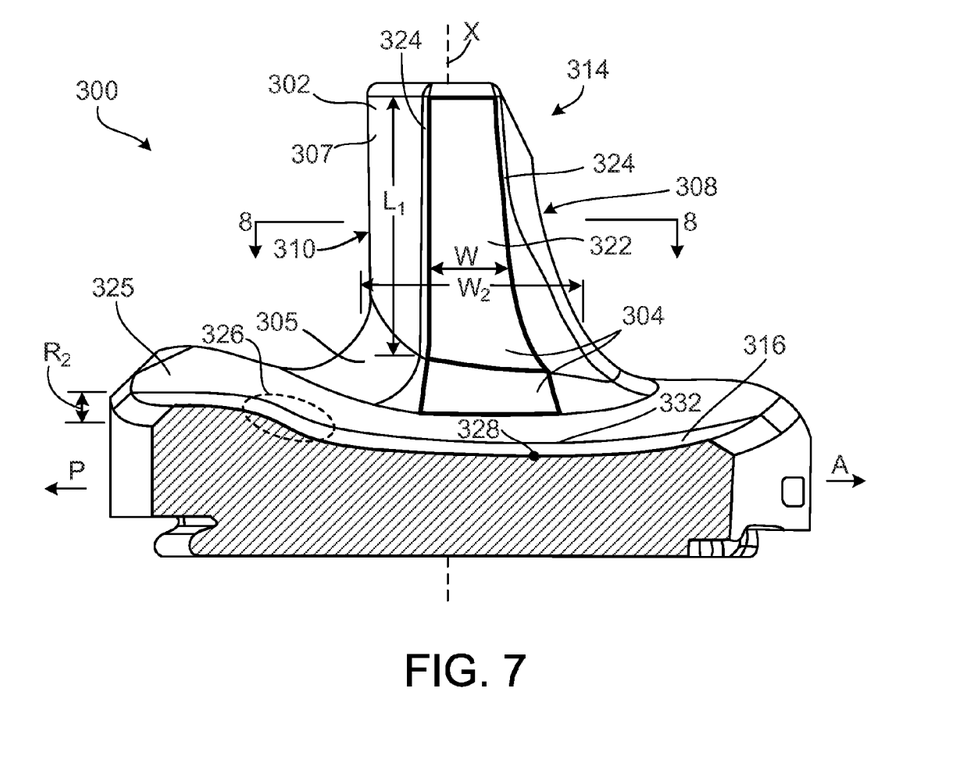
FIG. 7 is medial view of the tibial insert showing a cross section of a medial bearing surface.

Referring to FIGS. 6 and 7, the geometry of the tibial insert 300 permits and facilitates both tibiofemoral rotation and varus/valgus constraint. As noted above, the lateral surface 306 includes a contact section 320 (FIG. 6) and the medial surface 304 includes a contact section 322 (FIG. 7). These contact sections 320, 322 engage the walls 210, 211 of the femoral component 200 to provide varus/valgus constraint. To provide varus/valgus constraint and still permit tibiofemoral rotation at angles of flexion, for example, between extension (or hyperextension) and approximately 90 to 120 degrees, a total clearance of approximately 0.005 to approximately 0.030 inches is provided between the walls and the contact sections 320, 322. An increase in the clearance permits additional rotation, but lessens the varus/valgus constraint.

Figure 8:
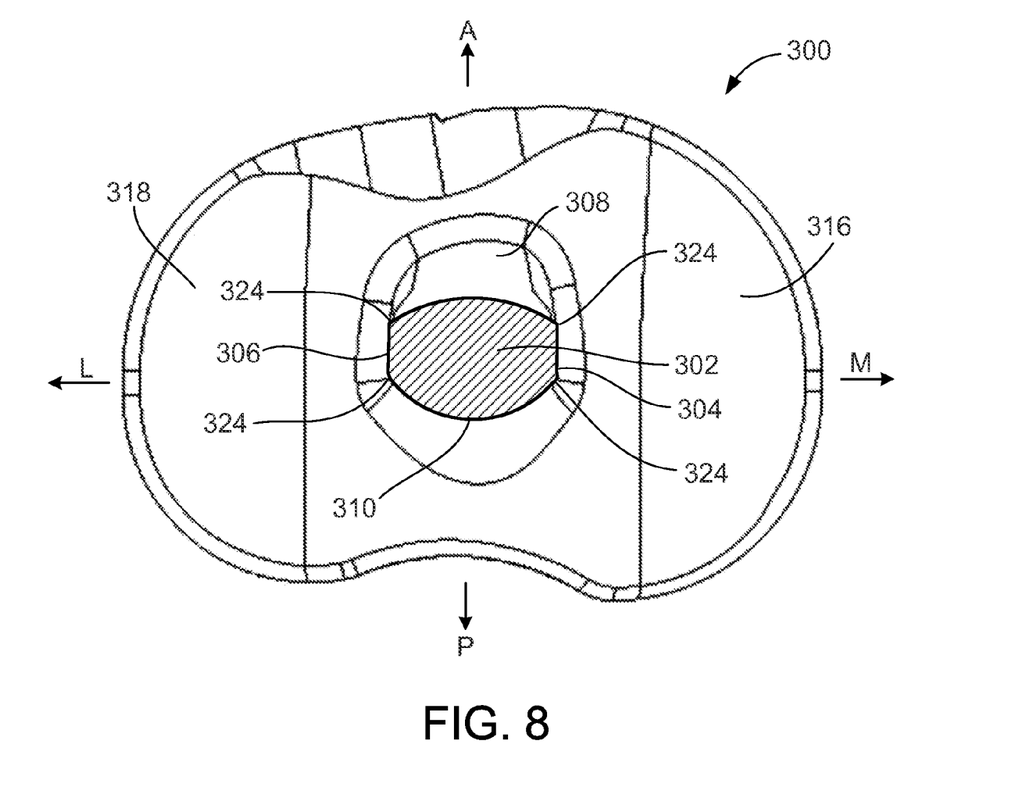
FIG. 8 is a top view of the tibial insert showing a sectional view of a tibial post across line 8-8 of FIGS. 6 and 7.

The post 302 includes rounded edges 324 as transitions from the medial surface 304 and lateral surface 306 to the anterior surface 308 and posterior surface 310 (also see FIG. 8). The rounded edges 324 extend substantially along a superior-inferior direction, and are rounded substantially in a transverse plane. When the post 302 rotates within the clearance provided between the post 302 and the walls 210, 211, the rounded edges 324 and portions of the anterior surface 308 and posterior surface 310 contact the walls 210, 211. The radius of the rounded edge can be, for example, between approximately 0.030 and 0.090 inches. A larger radius allows for more internal-external tibiofemoral rotation, but reduces the width, W, of the contact sections 320, 322 and the corresponding varus/valgus constraint. A smaller radius has the opposite effect.

The dimensions of the contact sections 320, 322 also permit an effective balance of varus/valgus constraint and tibiofemoral rotation. The greater the width of the contact sections 320, 322 in an anterior-posterior dimension, the greater the varus/valgus constraint but the less the tibiofemoral rotation. To achieve an appropriate balance, at various points along the axial length of the post 302, the width, W, of the contact sections 320, 322 can be between approximately one sixth and two thirds of the width, $W_2$, of the post 302. The width, $W_2$, can be the greatest width of the post 302 in an anterior-posterior direction at a particular axial height. Thus in some implementations, the contact sections 320, 322 extend such that, along at least half of the height, H, of the post 302, the width, W, of the contact sections 320, 322 at a given axial position is between one sixth and two thirds of a largest width (for example, $W_2$) of the post 302 at that axial position.

In some implementations, the relationship between an anterior-posterior width at a given axial position and the largest width at that axial position continues at portions of the medial surface 304 and the lateral surface 306 other than the contact sections 320, 322. For example, the width of the medial surface 304 and the width of the lateral surface 306 in an anterior-posterior direction can be between approximately one sixth and two thirds of the largest width of the post 302 in an anterior-posterior direction at positions along substantially the entire length of the medial surface 304 and the lateral surface 306 along the longitudinal axis, X, of the post 302.

The contact sections 320, 322 are substantially rectangular, to provide generally even contact area with the walls 210, 211. The greater the axial length of the contact sections 320, 322, the greater the varus/valgus control provided. In some implementations, the length of the contact sections 320, 322 along the axial direction of the contact sections 320, 322 is at least twice the width, W, of the contact sections 320, 322. For example, the average length of the contact sections 320, 322 can be more than twice the average width or maximum width of the contact sections 320, 322. Similarly, the average length of the medial surface 304 can be more than twice the average width or maximum width of the medial surface 304, and the average length of the lateral surface 306 can be more than twice the average width or maximum width of the lateral surface 306.

Differences between the lateral bearing surface 318 and the medial bearing surface 316 promote tibiofemoral rotation. The maximum depth or total depth, $R_1$ (FIG. 6), of the concave portion of the lateral bearing surface 318 is less than the maximum depth or total depth, $R_2$ (FIG. 7), of the concave portion of the medial bearing surface 316. In other words, the medial bearing surface 316 (FIG. 6) extends more inferior than the lateral bearing surface 318 (FIG. 7). Thus for an equal amount of force in a posterior direction, the resistance to translation is less on the side of the lateral bearing surface 316, resulting in greater translation of the lateral condylar portion 203 than the translation of the medial condylar portion 201.

In addition, the lateral bearing surface 318 includes a continuous concave portion 330 that extends along the lateral bearing surface 318 in an anterior-posterior direction, generally centered in the tibial insert 300. On the other hand, a concave portion 332 of the medial bearing surface 316, is offset from the center of the tibial insert in an anterior-posterior direction, so that the concave portion 332 is located more toward the anterior of the tibial insert 300. The medial bearing surface 316 includes a plateau or raised portion at a posterior portion 325 of the medial bearing surface 316. Adjacent to the posterior portion 325, the medial bearing surface 316 includes sloped section 326 having a relatively steep slope. For example, the medial concave portion 332 can have a slope at the sloped section 326 that is steeper than the slope of the lateral concave portion 330 at the same anterior-posterior position on the tibial insert 300. The sloped portion 326 can be steeper than the adjacent portions of the medial concave portion 332 and can be steepest portion of the medial concave portion 332 along the anterior-posterior direction. The sloped section 326 can engage the medial condylar surface 202 to limit posterior travel of the medial condylar surface 202 during flexion.

To further promote lateral travel of the lateral condylar portion 201, a bottom point or equilibrium point 327 (FIG. 6) (for example, indicating the most planar section of the lateral bearing surface 318) is located anterior to the center of the post 302 on the lateral bearing surface 318. An equilibrium point 328 (FIG. 7) of the medial bearing surface 316 is located generally at the same anterior position as the lateral equilibrium point 327. The condylar portions 201, 203 generally follow the slopes of the bearing surfaces 316, 318, which without other forces, would lead the condylar portions 201, 203 to the respective equilibrium points 327, 328. This relationship between the anterior-posterior position of the equilibrium points 327, 328 guides the femoral condylar portions 201, 203 to roughly the same anterior-posterior position when the knee is extended. Also, the position of the equilibrium points 327, 328 allows the lateral femoral condylar portion 203 to move more anterior than the medial condylar portion 201 as the knee extends, as occurs in a native knee due to the "screw home" mechanism.

Figure 9:
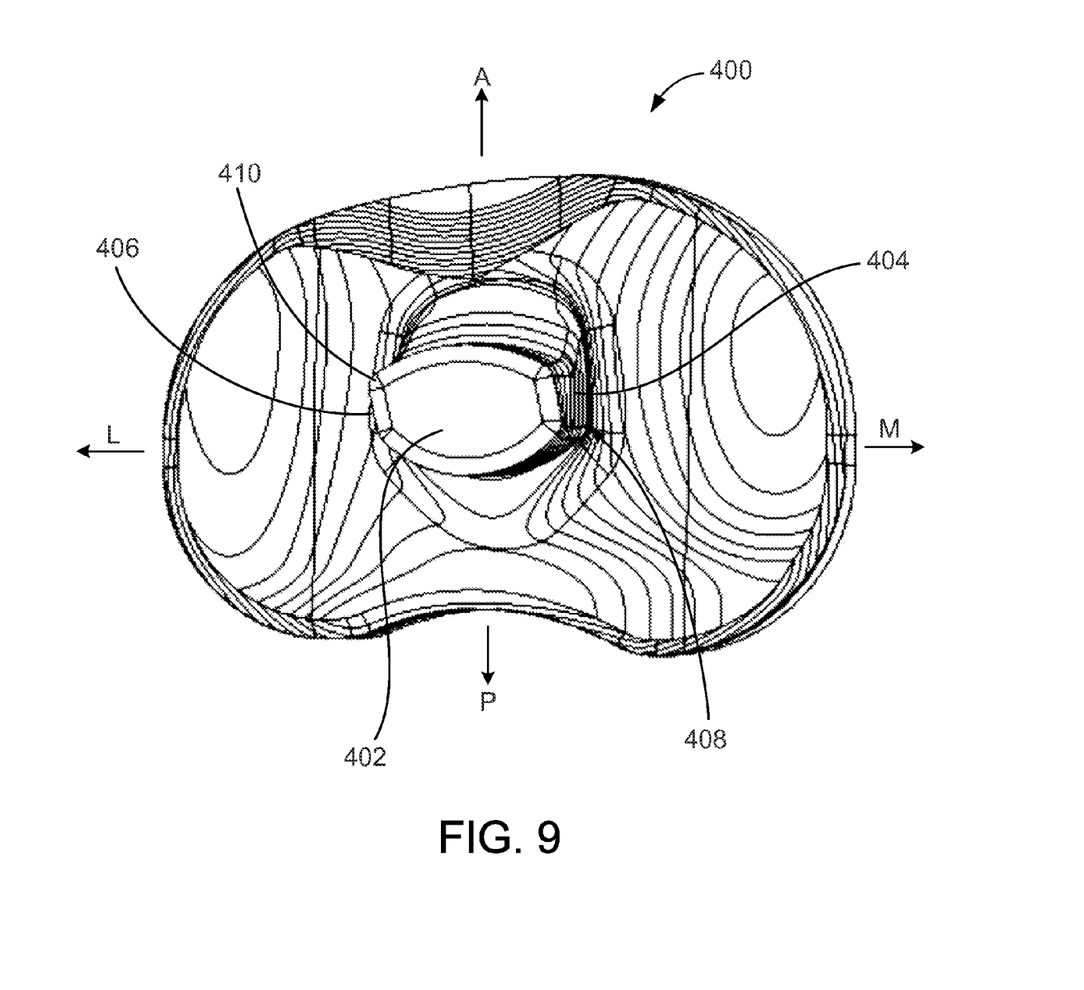
FIG. 9 is a top view of a tibial insert for a left knee with a laterally rotated tibial post.

Referring to FIG. 9, in an alternate implementation of a tibial insert 400, the tibial insert 400 includes a post 402 that is twisted along the longitudinal axis of the post 402. As a result, a medial surface 404 and a lateral surface 406 are offset from an anterior-posterior alignment, and a superior portion of the post 402 is rotationally offset from an inferior portion of the post 402. Alternatively, the post 402 can be rotated instead of twisted. For example, a post can be rotationally offset from a base such that the medial surface and the lateral surface are both oriented at an angle with respect to medial and lateral sides of the base from which the post extends. A twisted or rotated post can permit more internal tibial rotation in flexion than the non-rotated implementation without as much of a reduction in varus/valgus constraint.

The medial surface 404 and the lateral surface 406 can include substantially flat portions or other portions configured to contact the walls 210, 211 of the femoral component 200, described above, to provide varus/valgus constraint while allowing tibiofemoral rotation. For example, the medial surface 404 and lateral surface 406 are substantially parallel to each other. As another example, as the femoral component 200 flexes with respect to the tibial insert 400, the walls 210, 211 follow the twist of the medial surface 404 and the lateral surface 406 to provide tibiofemoral rotation. In extension, the medial posterior edge 408 and the lateral anterior edge 410 contact the walls 210, 211 to provide varus/valgus constraint. Other portions of the medial surface 404 and the lateral surface 406 also engage the walls 210, 211 to provide varus/valgus constraint.

A number of implementations and alternatives have been described. Nevertheless, it will be understood that various modifications may be made without departing from the spirit and scope of the disclosure. Accordingly, other implementations are within the scope of the following claims.

What is claimed is:

1. A prosthesis comprising:
a femoral component that defines an opening between parallel inner walls; and
a tibial insert having a base and a post extending from the base, the post having a medial surface and a lateral surface and being configured to be received in the opening,
the medial surface having a medial contact surface, and the lateral surface having a lateral contact surface oriented parallel to the medial contact surface,
the medial contact surface and the lateral contact surface each having a width in an anterior-posterior direction that is sufficient to constrain varus/valgus alignment of the prosthesis over a flexion/extension range from extension to a position between 90 to 120 degrees of flexion when the tibial insert is mated with the femoral component such that the post is received in the opening and the medial contact surface and the lateral contact surface each engage one of the parallel inner walls,
wherein engagement of the tibial insert and the femoral component rotates the tibial insert relative to the femoral component over at least a portion of the constrained flexion/extension range.

2. The prosthesis of claim 1, wherein the post is dimensioned to provide a total clearance of 0.005 inches to 0.030 inches between the post and the parallel inner walls when the post is received in the opening.

3. The prosthesis of claim 1, wherein the post has a posterior surface and an anterior surface, and the post has rounded edges between the anterior surface and the medial and lateral surfaces and between the posterior surface and the medial and lateral surfaces.

4. The prosthesis of claim 1, wherein the base has a medial bearing surface having a concave portion and a lateral bearing surface having a concave portion,
the concave portion of the medial bearing surface being positioned anteriorly offset from a center of the base and having a maximum depth in a superior-inferior direction that is more inferior than a maximum depth of the concave portion of the lateral bearing surface in the superior-inferior direction.

5. The prosthesis of claim 1, wherein:
the post has a posterior surface; and
the femoral component has an asymmetrical posterior cam configured to engage the posterior surface to drive rotation of the tibial insert relative to the femoral component.

6. The prosthesis of claim 5, wherein the posterior cam is configured to engage the posterior surface at angles of flexion that are greater than a first angle that is between 60 and 90 degrees of flexion, and the posterior cam is configured to not engage the posterior surface at angles of flexion less than the first angle.

7. The prosthesis of claim 1, wherein the post has a proximal surface that is flat and a notch defined in a superior anterior portion of the post, wherein at least a portion of the notch is defined completely through the post along a medial-lateral direction.

8. The prosthesis of claim 1, wherein the medial contact surface and the lateral contact surface are flat and are oriented along the anterior-posterior direction.

9. The prosthesis of claim 1, wherein the post is twisted along an axis of the post such that a superior portion of the post is rotationally offset from an inferior portion of the post.

10. The prosthesis of claim 1, wherein the post is rotationally offset from the base such that the medial surface and the lateral surface are oriented at an angle with respect to medial and lateral sides of the base.

11. The prosthesis of claim 1, wherein the post has an anterior surface and a posterior surface, and the anterior surface and the posterior surface each have a convex portion.

12. The prosthesis of claim 1, wherein the base of the tibial insert has a medial bearing surface having a medial concave portion and a lateral bearing surface having a lateral concave portion, and wherein the medial concave portion has a sloped section at a posterior region and the sloped portion has a steeper slope in the anterior-posterior direction than adjacent portions of the medial concave portion.

13. The prosthesis of claim 12, wherein the sloped section has a slope that is steeper than a slope of the lateral concave portion at the same anterior-posterior position on the tibial insert.

14. The prosthesis of claim 12, wherein the sloped portion is a steepest portion of the medial concave portion along the anterior-posterior direction.

15. The prosthesis of claim 12, wherein the femoral component has a medial condylar surface, and wherein the sloped section is configured to engage the medial condylar surface to limit posterior travel of the medial condylar surface during flexion.

16. The prosthesis of claim 1, wherein the base of the tibial insert has a medial bearing surface having a medial concave portion and a lateral bearing surface having a lateral concave portion, and wherein the medial concave portion and the lateral concave portion each have an equilibrium region that engages femoral condylar regions at full extension, the equilibrium regions being located at the same anterior-posterior position.

17. The prosthesis of claim 16, wherein the medial equilibrium region is a most inferior region along the medial concave portion, and wherein the lateral equilibrium region is a most inferior region along the lateral concave portion.

18. The prosthesis of claim 16, wherein the medial equilibrium region is a most planar section of the medial concave portion, and the lateral equilibrium region is a most planar section of the lateral concave portion.

19. The prosthesis of claim 1, wherein the femoral component comprises a medial condylar portion and a lateral condylar portion, and wherein the base of the tibial insert is shaped to engage the condylar portions such that the lateral condylar portion experiences greater anterior movement than the medial condylar portion as the prosthesis moves from flexion to extension.

20. The prosthesis of claim 1, wherein the post has a height along a superior-inferior axis, and wherein, along a majority of the height of the post, a medial-lateral width between the medial contact surface and the lateral contact surface is a widest medial-lateral width of the post.

21. A prosthesis comprising:
a femoral component that defines an opening between parallel inner walls; and
a tibial insert having a base and a post extending from the base, the post having a medial surface and a lateral surface and being configured to be received in the opening,
the medial surface having a medial contact surface, and the lateral surface having a lateral contact surface oriented parallel to the medial contact surface,
the medial contact surface and the lateral contact surface each having a width in an anterior-posterior direction that is sufficient to constrain varus/valgus alignment of the prosthesis over a flexion/extension range from extension to a position between 90 to 120 degrees of flexion when the tibial insert is mated with the femoral component such that the post is received in the opening and the medial contact surface and the lateral contact surface each engage one of the parallel inner walls,
wherein engagement of the tibial insert and the femoral component rotates the tibial insert relative to the femoral component over at least a portion of the constrained flexion/extension range,
wherein the base of the tibial insert has a medial bearing surface having a medial concave portion and a lateral bearing surface having a lateral concave portion, and wherein the medial concave portion has a sloped section at a posterior region and the sloped portion has a steeper slope in the anterior-posterior direction than adjacent portions of the medial concave portion.

22. A prosthesis comprising:
a femoral component that defines an opening between parallel inner walls; and
a tibial insert having a base and a post extending from the base, the post having a medial surface and a lateral surface and being configured to be received in the opening,
the medial surface having a medial contact surface, and the lateral surface having a lateral contact surface oriented parallel to the medial contact surface,
the medial contact surface and the lateral contact surface each having a width in an anterior-posterior direction that is sufficient to constrain varus/valgus alignment of the prosthesis over a flexion/extension range from extension to a position between 90 to 120 degrees of flexion when the tibial insert is mated with the femoral component such that the post is received in the opening and the medial contact surface and the lateral contact surface each engage one of the parallel inner walls,
wherein engagement of the tibial insert and the femoral component rotates the tibial insert relative to the femoral component over at least a portion of the constrained flexion/extension range,
wherein the base of the tibial insert has a medial bearing surface having a medial concave portion and a lateral bearing surface having a lateral concave portion, and wherein the medial concave portion and the lateral concave portion each have an equilibrium region that engages femoral condylar regions at full extension, the equilibrium regions being located at the same anterior-posterior position.

* * * * *